United States Patent [19]
Petschek et al.

[11] Patent Number: 5,389,339
[45] Date of Patent: Feb. 14, 1995

[54] INTEGRAL BIOMOLECULE PREPARATION DEVICE

[75] Inventors: Harry E. Petschek, Lexington, Mass.; Henry Kaufmann, Danville, N.H.; Robert A. Quinlan; David A. DeBonville, both of Beverly, Mass.; Martin J. Sklar, Needham, Mass.; Ronald D. Danehy, Tewksbury, Mass.; Michael Foley, Beverly, Mass.; John McG. Dobbs; David Banks, both of South Hamilton, Mass.

[73] Assignee: Enprotech Corporation, New York, N.Y.

[21] Appl. No.: 932,285

[22] Filed: Aug. 19, 1992

Related U.S. Application Data

[63] Continuation of Ser. No. 517,221, May 1, 1990, abandoned.

[51] Int. Cl.⁶ .................. G01N 35/00; G01N 35/06
[52] U.S. Cl. ......................... 422/64; 422/67; 422/72; 422/116; 935/87; 935/88
[58] Field of Search .......... 422/63, 64, 67, 72, 422/100, 101, 116; 436/45, 54, 174, 175, 177, 178, 180; 935/87, 88

[56] References Cited

U.S. PATENT DOCUMENTS

| | | | |
|---|---|---|---|
| 4,252,769 | 2/1981 | Hood et al. | 422/50 |
| 4,340,390 | 7/1982 | Collins et al. | 422/64 X |
| 4,341,736 | 7/1982 | Drbal et al. | 422/64 X |
| 4,344,768 | 8/1982 | Parker et al. | 422/100 X |
| 4,436,822 | 3/1984 | Eseifan | 422/64 X |
| 4,451,433 | 5/1984 | Yamashita et al. | 422/64 X |
| 4,598,049 | 7/1986 | Zelinka et al. | 935/88 X |
| 4,795,710 | 1/1989 | Muszak et al. | 422/64 X |
| 4,808,380 | 2/1989 | Minekane | 422/64 |
| 4,908,186 | 3/1990 | Sakamaki | 422/64 |
| 5,122,343 | 6/1992 | Ishizaka et al. | 422/65 X |

FOREIGN PATENT DOCUMENTS

| | | |
|---|---|---|
| 0122772 | 10/1984 | European Pat. Off. |
| 0187699 | 7/1986 | European Pat. Off. |
| 0316766 | 5/1989 | European Pat. Off. |
| 2283279 | 11/1990 | Japan |

OTHER PUBLICATIONS

T. Maniatis et al., "Molecular Cloning: A Laboratory Manual", Cold Spring Harbor Laboratory, 1982.

*Primary Examiner*—Jeffrey R. Sway
*Attorney, Agent, or Firm*—Brian M. Dingman

[57] ABSTRACT

An integral biomolecule preparation device which accomplishes all of the nucleic acid separation steps, including centrifugation, reagent addition, and pipeting, automatically without human intervention to fully automate the DNA separation procedure.

43 Claims, 10 Drawing Sheets

PROCESS VARIABLES

| COMMAND | VARIABLES (Inputs) |
|---|---|
| 1. Spin Centrifuge | Speed, (rpm), time (sec.) |
| 2. Add Reagent | Reagent (A–L), amount ($\mu l$), tube (A, B or C) |
| 3. Pipet Mix | Tube (A, B or C), pipet position ($\mu l$), volume ($\mu l$), pipet rate ($\mu l$/sec), repititions (number) |
| 4. Bubble Mix | Tube (A, B or C), pipet position ($\mu l$), volume ($\mu l$), bubble rate ($\mu l$/sec.), repititions (number) |
| 5. Pick Pipet | Tip (A, B or C) |
| 6. Park Pipet | N/A |
| 7. Withdraw | Tube (A, B or C), pipet position ($\mu l$), volume ($\mu l$), pipet rate ($\mu l$/sec), mode (fixed or variable) |
| 8. Dispense | Tube (A, B or C), pipet position ($\mu l$), volume ($\mu l$), dispense rate ($\mu l$/sec) |

*Fig. 3A*

PROCESS VARIABLES

| COMMAND | VARIABLES (Inputs) |
|---|---|
| 9. Puff | Volume ($\mu$l) |
| 10. Dispose of Fluid | N/A |
| 11. Wait | Time (number of time periods) |
| 12. Delay | Time (seconds) |
| 13. Begin | N/A |
| 14. Next Sample | N/A |
| 15. Overlap | N/A |

*Fig. 3B*

INTEGRAL BIOMOLECULE PREPARATION DEVICE

This is a continuation of application Ser. No. 07/517,221, filed May 1, 1990, now abandoned.

FIELD OF INVENTION

This invention relates to an integral biomolecule preparation device which automatically prepares DNA from samples.

BACKGROUND OF INVENTION

The preparation of biomolecules, for example the separation of DNA from prokaryotic, eukaryotic and viral cultures, is an extremely precise, time-consuming operation which requires hours of skilled technician's time. Several procedures commonly used are disclosed in T. Maniatis et al., *Molecular Cloning-A Laboratory Manual*, Cold Spring Harbor Laboratory (1989).

These well known procedures are typically performed essentially manually. The technician adds the necessary reagents by pipeting, may accomplish the mixing by hand or with a vortex mixer, and may employ a fixed-speed centrifuge to perform the separations and pelleting. These procedures are not only time consuming, but because of the nature and extent of the technician's involvement, are prone to human error. As a result, the cost per separation is relatively high.

There exist numerous mechanical devices for performing some or all of the individual steps of these preparation techniques. For example, automated pipeting machines may be employed to relatively quickly and accurately add the desired reagents to the sample tubes. Separate mixing machines such as test tube inverters may also be used to accomplish some of the mixing steps. However, even if this process automating equipment is used, the entire preparation procedure still requires a relatively large number of distinct steps, each requiring at least a technician's guidance. Hence, the mechanical devices do not substantially reduce the cost per separation.

SUMMARY OF INVENTION

It is therefore an object of this invention to provide a biomolecule preparation device which may be used to prepare a variety of biomolecules (e.g. proteins, DNA, RNA, etc.) from a variety of sources (e.g. cells, tissue, polymerase chain reaction products, etc.).

It is a further object of this invention to provide such an apparatus which automatically extracts and pellets nucleic acid from cell samples without human intervention.

It is a further object of this invention to provide such an apparatus which can automatically process many (for example twelve) samples in approximately one hour.

It is a further object of this invention to provide such an apparatus in which the separated nucleic acid is at least as pure as that provided by the manual methods.

It is a further object of this invention to provide such an apparatus in which consistent nucleic acid separation results are repeatedly obtained without human intervention.

This invention results from the realization that a fully automated biomolecule preparation procedure may be accomplished with an integral device which accomplishes all of the reagent addition, mixing, pipeting, and centrifugation necessary to separate DNA from cells.

This invention features an integral device for automatically preparing biomolecules such as nucleic acid from sources such as cell samples, including a centrifuge for spinning cell sample tubes in its rotor, a pipet tip rack for holding a number of pipet tips, and a pipet arm for removing the pipet tips from the rack and inserting them into the sample tubes. Further included are means for withdrawing fluid from a sample into the inserted pipet tip, means for mixing the tube contents, a number of reagent reservoirs for holding the preparation reagents, and means for adding controlled amounts of the reagents to the sample tubes. Finally, there is included means for maintaining a predetermine relationship between the pipet tips and the sample tubes to prevent contamination.

Preferably, the means for maintaining includes means for controlling the relative positions of the rotor and the pipet tip rack. In that case, the means for controlling may include means for determining the position of the pipet tip rack and/or the position of the rotor, in which case means for rotating the rotor and/or the rack may be included, which means are responsive to the means for determining the position of the rotor or rack, respectively, for properly positioning the pipet tips in relation to the sample tubes. The rotation may be accomplished with a stepper motor for indexing the rotor or rack.

Preferably, for most of the steps of the nucleic acid separation protocols, a single pipet tip is used with a single cell sample tube to prevent cross-contamination. In a preferred embodiment, the centrifuge rotor is rotated with a brushless DC motor which includes a detent position for each rotor sample tube location. The separation device preferably further includes means for controlling the speed and duration of rotation of the centrifuge rotor.

Preferably, the means for adding reagents includes at least one reagent dispensing opening fixed in relation to the rotor to allow positioning of a selected sample tube below a selected dispensing opening. In a preferred embodiment, the means for maintaining includes means for aligning a selected pipet tip with a selected sample tube. In that case, there may further be included means for moving the pipet arm in two axes, one axis in and out of the rotor and pipet tip rack, and one between the rotor and the pipet tip rack, to allow the pipet tips to be removed from the rack, placed in a sample tube, and placed back in the rack with only a two axis movement device. Alternatively, the pipet arm may move in three dimensions; in that case the pipet tip rack could be fixed. Preferably, the pipet arm is moved with at least one stepper motor for control the positioning the pipeting end. In that case, there are further included means for sensing a neutral position of the stepper motor to maintain position control of the device being moved.

The device also preferably includes means for stripping a pipet tip from the pipet arm, which may be accomplished by including a stripping structure proximate each pipet tip position in the pipet tip rack.

The means for withdrawing fluid from the sample tubes preferably includes an air cylinder operably connected to the pipet arm pipetting end. The air cylinder may include a movable piston for varying the volume of the air cylinder, along with means for controllably moving the piston, which may also be accomplished with a stepper motor with means for sensing its neutral position. The means for mixing the tube contents may include means for dispensing withdrawn fluid back into the sample tube. In that case, the fluid flow rate is preferably controllable for controlling the mixing shear. An alternative means for mixing may include means for agitating the centrifuge rotor.

The means for adding reagents to the sample tubes preferably includes a reagent delivery orifice for delivering reagents at predetermined flow rate. In that case, there may further be included means for controlling the reagent pressure to deliver reagent through the orifice at a controllable rate and delivery force for mixing the sample tube contents. The volume of reagent added may then be controlled by controlling the reagent delivery period.

The separation device also preferably includes means for determining the reagent volume in the reagent reservoirs. This may be accomplished with level sensors such as capacitive type sensors, or by including means for supplying a known volume of gas at a known pressure to the reservoir to determine the amount of empty space in the reagent reservoir.

In another preferred embodiment, the means for adding reagents includes a liquid delivery conduit from the reservoirs leading to the centrifuge rotor including a means for sensing the presence of reagent proximate the end of the delivery conduit, which may be accomplished by determining a change in light intensity transmitted through the conduit. Preferably, the conduit includes a relatively large diameter, substantially vertical portion, for allowing trapped air bubbles to escape to allow precise control of reagent volume. There is also preferably included means for withdrawing reagent from the conduit after reagent delivery to prevent reagent spillage.

In another embodiment, the pipet arm includes a stepper motor for controllably inserting the pipeting end into the pipet tips. The pipet arm may also include means for controlling the depth of insertion of the pipet tip into the sample tube, and means for determining the liquid level height in the sample tube. In that case, the means for controlling the depth of insertion is preferably responsive to the determined liquid level height for placing the pipet tip at a desired position in relation to the tube liquid surface.

DISCLOSURE OF PREFERRED EMBODIMENT

Other objects, features and advantages will occur to those skilled in the art from the following description of a preferred embodiment and the accompanying drawings, in which:

FIGS. 3A and 3B are a list of preferred software process commands and associated inputs for the device of this invention;

Figures 5A, 5C:
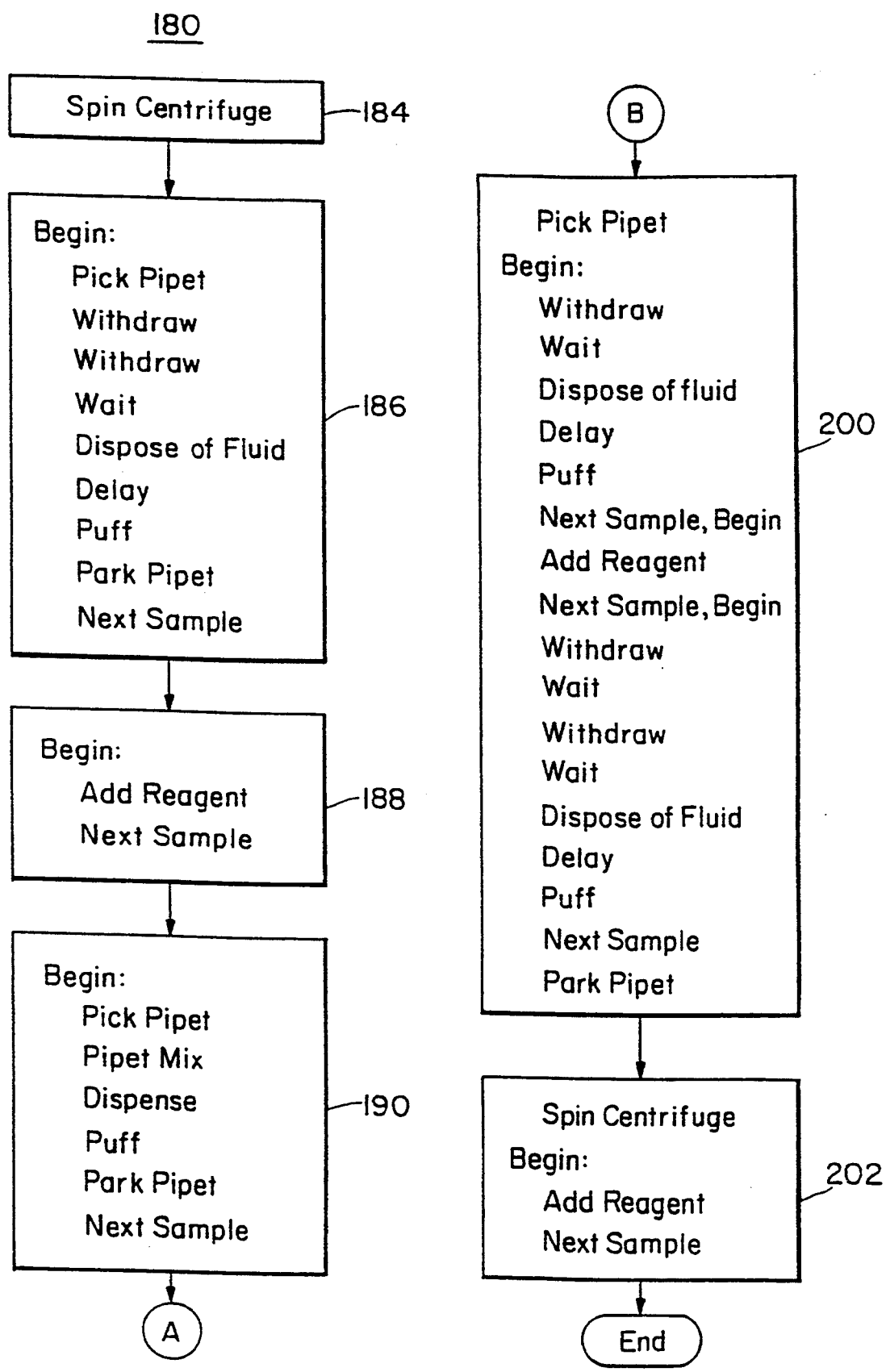

FIGS. 5A, B and C together are an embodiment of a DNA separation process performed by the preparation device according to this invention.

This invention may be accomplished in a biomolecule preparation device which automatically performs all of the preparation steps—reagent addition, mixing pipeting, and centrifugation—necessary to fully automate the preparation of biomolecules such as proteins and nucleic acids from samples such as suspensions and cell samples. The device automates those preparation procedures known in the art, as well as customized preparation procedures developed by the user. In a preferred embodiment of the device, DNA separation from cell samples is performed.

Figure 1A:
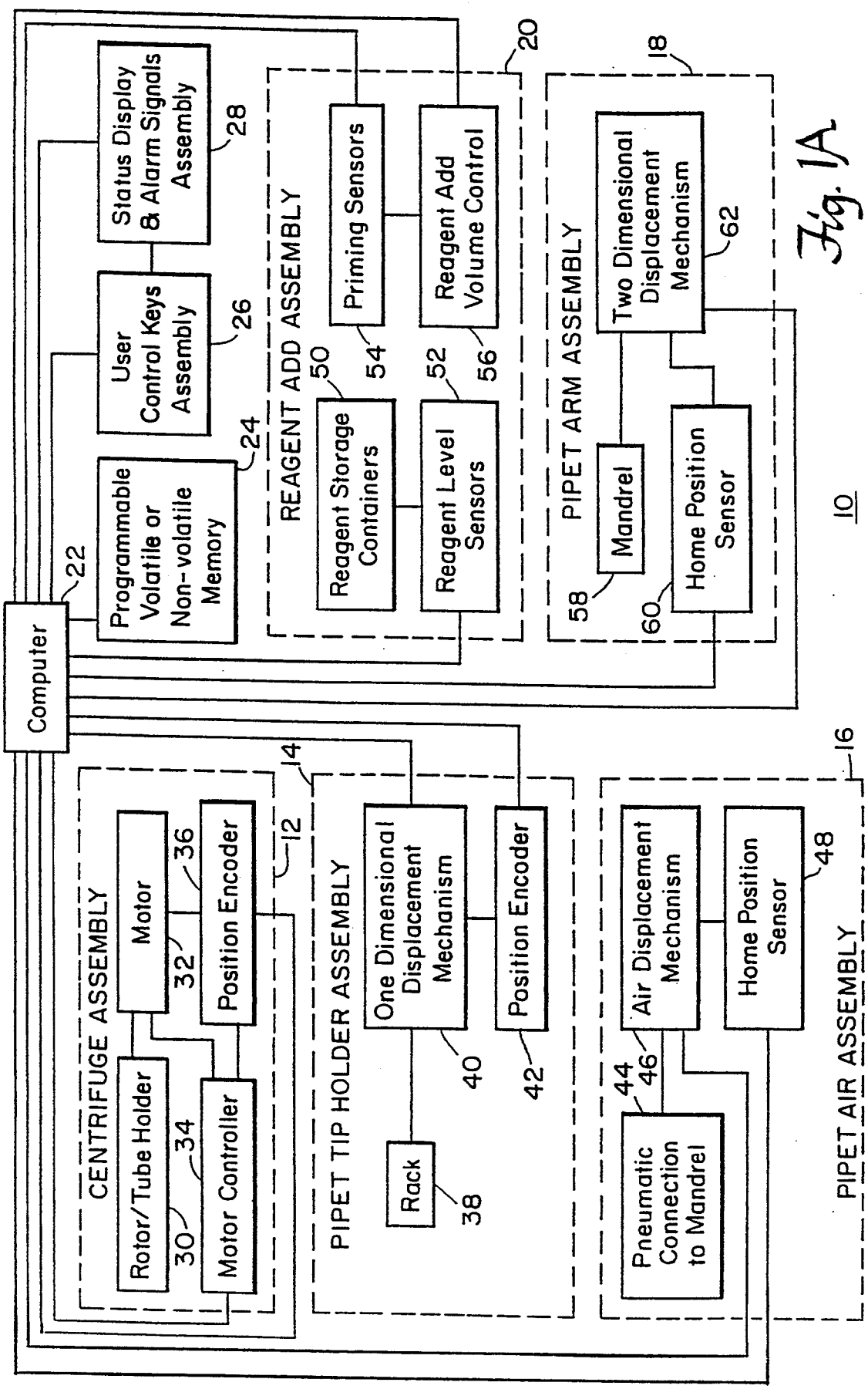
FIG. 1A is a block diagram of the biomolecule preparation device according to this invention.

There is shown in FIG. 1A integral biomolecule preparation device 10 according to this invention, which is described in accordance with a nucleic acid separation procedure. Device 10 includes centrifuge assembly 12, pipet tip rack or holder assembly 14, pipet air assembly 16, reagent add system assembly 20, and pipet arm assembly 18. Computer 22 in conjunction with memory 24 controls the operation of the assemblies as will be described with more particularity below. User control keys assembly 26 allows the device user to input the process variables described in conjunction with FIGS. 3A and 3B. Status display and alarm signal assembly 28 may be used to display the status of the device (for example, the step in process), and/or display or signal an alarm (for example, indicating a problem with a device assembly, or a low liquid level). Device 10 includes in total all the process assemblies necessary to allow the device to be used to automatically perform nucleic acid separation procedures without human intervention.

Centrifuge assembly 12 includes motor 32, for both spinning and indexing rotor/sample tube holder 30, controlled by motor controller 34. Controller 34 is responsive to rotor position encoder 36 for positioning rotor 30 where desired under the control of computer 22.

Pipet tip rack assembly 14 includes pipet rack 38 driven by one dimensional displacement mechanism 40, responsive to computer 22. Position encoder 42 determines the position of rack 38 to allow computer 22 to properly control mechanism 40 to place rack 38 in a desired position. As a result of the positioning mechanisms of assemblies 12 and 14, device 10 provides the ability to keep track of the sample tube and pipet tip in current use. This feature is typically used to insure that a single pipet tip is employed for each sample tube in order to prevent sample contamination.

Pipet arm assembly 18 includes mandrel 58 driven to move in two dimensions by mechanism 62. Sensors 60 pass information relating to the position of mandrel 58 to computer 22 for use in controlling displacement mechanism 62 to place mandrel 58 where desired. This provides the ability of assembly 18 to remove a pipet tip from rack 38, insert it in a sample tube in rotor 30 to a desired depth, and place the pipet tip back into rack 38.

Pipet air assembly 16 is employed to withdraw and/or dispense fluid from the pipet tip on mandrel 58, or to mix sample tube contents, employing air displacement mechanism 46 connected to mandrel 58 by connecting device 44. Sensor 48 passes information relating to the air volume in displacement mechanism 46 to computer 22 for use in controlling mechanism 46.

Reagent add assembly 20 accomplishes the addition of one or more reagents to the sample tubes in rotor 30 employing reagent add volume control 56 driven by computer 22, also responsive to priming sensors 54, which determine when the reagent fill lines are properly primed, as will become apparent below. Reagent storage containers 50 having reagent level sensors 52, which may be liquid level sensors such as capacitive type sensors, or floats. Reagent volume may alternatively be determined by measuring the volume of empty space in the reservoirs as described below.

Figure 1B:
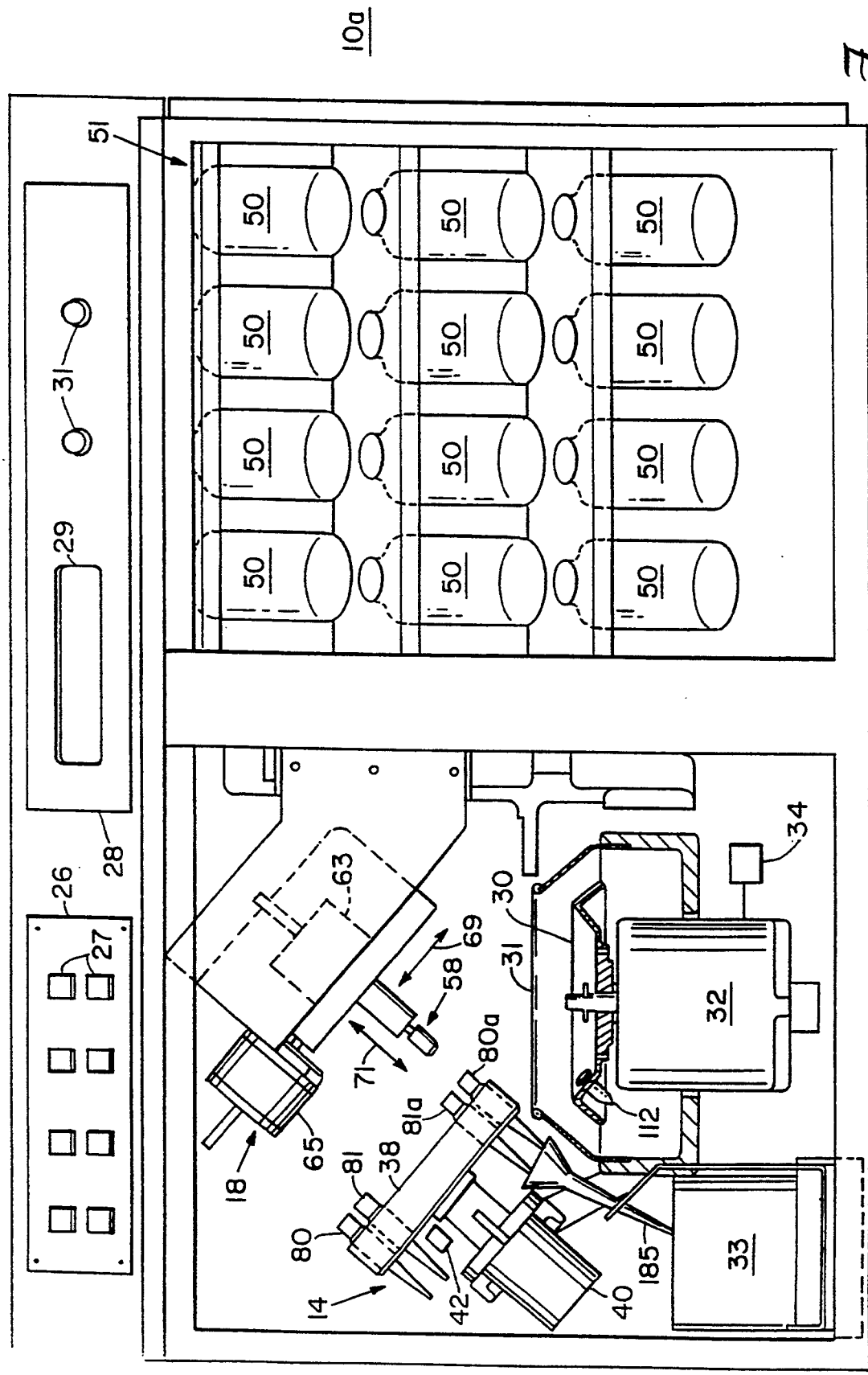
FIG. 1B is a schematic diagram of a preferred embodiment of the device of FIG. 1A.

Fig. 1B illustrates schematically a front view of one embodiment of nucleic acid separation device 10a according to this invention. Twelve-reagent bottles 50 are mounted on one side of cabinet 51. The details of the reagent feed system for feeding liquids from storage containers 50 to the sample tubes in centrifuge rotor 30 are described and shown in detail below in conjunction with FIG. 2E. Centrifuge motor 32 is preferably a variable speed, brushless DC motor having eight poles, so that it naturally has 24 equally circumferentially spaced detent positions. This allows the centrifuge motor to also be used to index singly a 24-tube rotor, sufficient for processing twelve cell samples. Motor 32 is responsive to motor controller 34, which itself is responsive to computer 22 (not shown) for controlling the rotational speed of rotor 30, the rotor rotation time, as well as the position of rotor 30 in relation to pipet tip engaging mandrel 58, as is described with more particularity in conjunction with FIG. 2C, and in relation to reagent add nozzles 126, FIG. 2E.

Similarly, pipet tip rack assembly 14 includes indexing stepper motor 40 for rotating disc-shaped pipet tip rack 38 to present the desired pipet tip 80 or 81 to mandrel 58. Rotor position encoder 42 feeds the rotor position to computer 22 to allow the computer to ensure that the desired pipet tip is presented to mandrel 58 for use with the desired sample tube in rotor 30. Rotor 30 is surrounded by safety containment shield 31, necessary for a high-speed centrifuge.

Pipet arm assembly 18 includes pipet tip engaging mandrel 58, movable in two dimensions; motor 65 drives mandrel 58 in the direction of arrow 69 and motor 63 drives mandrel 58 in the direction of arrow 71.

When system 10a is enabled to withdraw a pipet tip 80 and insert it in a sample tube, such as tube 112 in rotor 30, motor 63 engages mandrel 58 with tip 80 and then reverses direction to withdraw the tip from rack 38. Motor 65 then moves mandrel 58 in the direction of arrow 69 to align the mandrel and engaged pipet tip with the sample tube in the home position; tips 80 and 81 and tube 112 in the rack and rotor home positions are parallel, so that a two dimensional pipet tip displacement mechanism may be employed. Motor 63 then controls the movement of mandrel 58 to place the pipet tip at a desired position in sample tube 112 to perform a pipeting operation as is further described below. Waste fluid from sample tubes is disposed of in waste container 33 employing funnel 185 for directing fluid from the pipet tip 80a or 81a in the pick up position into container 33.

An alternative arrangement of rotor 30 and rack 38, in which the centrifuge motor can be employed to step both the rotor and pipet tip rack, contemplates an arrangement in which the centrifuge includes an elongated vertical shaft, and pipet tip rack 38 is placed on that shaft. Then, when the centrifuge is indexed, the pipet tip rack is indexed at the same time, maintaining the pipet tip-sample tube relationship. With this arrangement, in order to centrifuge the samples, the pipet tip rack is simply lifted off of the centrifuge, and placed back on after centrifugation. Proper initial positioning of the centrifuge rotor in relation to the pipet tip rack may be accomplished by stepping the centrifuge before the pipet tip rack is placed thereon to maintain correspondence between the pipet tips and the sample tubes as has been described.

User control keys assembly 26 and status display and alarm signal assembly 28 are also shown schematically in FIG. 1B. Assembly 26 includes a plurality of keys 27 which allow the user to enter information into the system as further described below. Assembly 28 may include CRT or LCD read-out 29 for prompting the user and/or indicating system conditions, such as the process step being performed, or the reagent levels. Status or alarm signals or lights 31 may be included for signalling one or more of those conditions as desired.

Figure 2A:
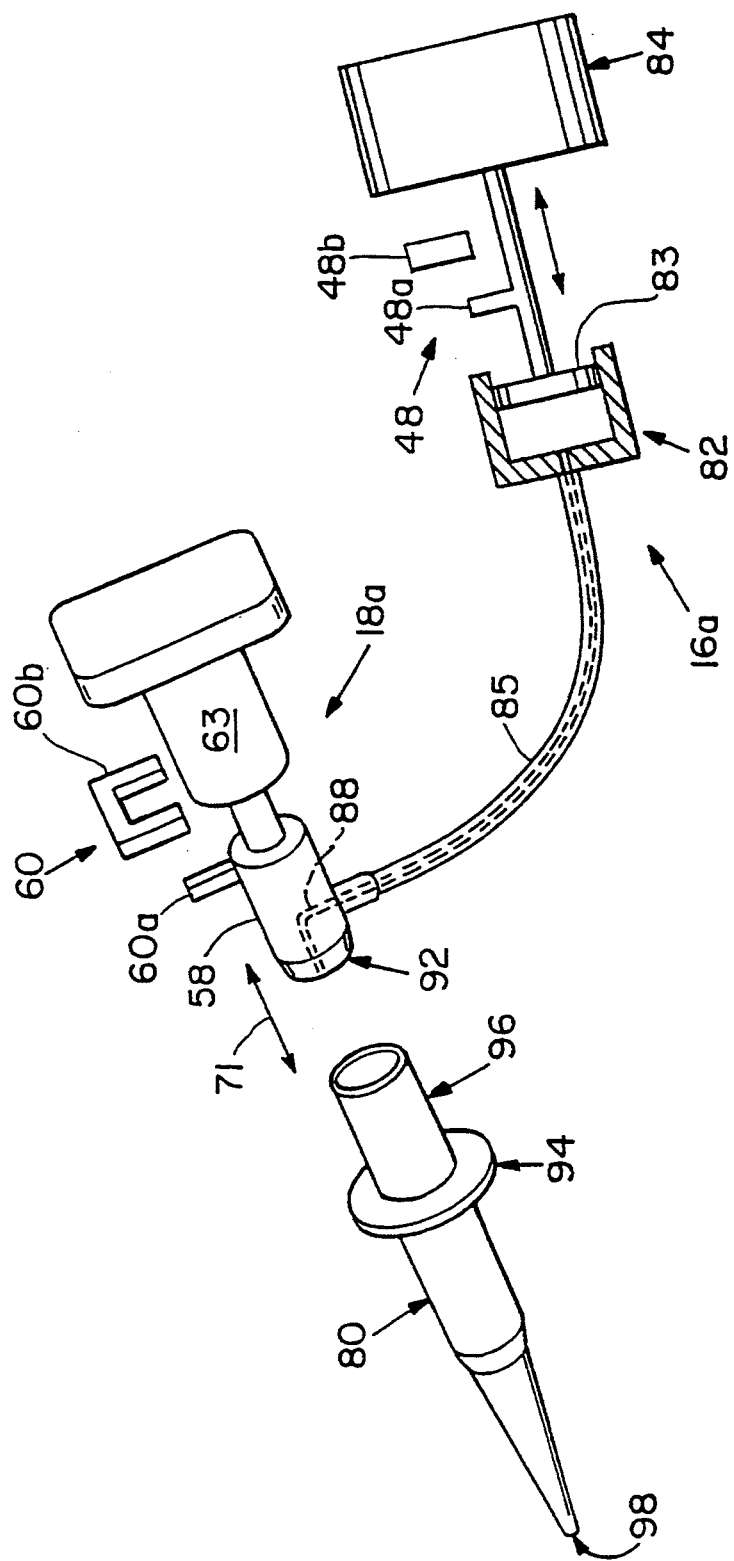
FIG. 2A is a detailed schematic diagram of an embodiment of the pipet tip holder and pipet air device of FIG. 1A.

FIG. 2A illustrates partially and in more detail the operation of pipet air assembly 16a and pipet arm assembly 18a. Position sensors 60 and 48 consist of an interrupter flag 60a or 48a which moves with the mandrel or pipet air piston and interrupts a fixed light beam passed across the ends of the U-shaped LED sensor combination 60b or 48b. Recording the position at which the flag interrupts the light beam defines a neutral or home position for the mandrel or piston. Other positions are then tracked by counting steps of the stepper motor away from the home position. The home position is rechecked periodically, in case of loss of steps, by passing through the home position and updating the computer.

Mandrel 58 includes tapered section 92 for engaging upper conical portion 96 of pipet tip 80 having dispensing opening 98. Also included is tubular passage 88 for connecting mandrel 58 to air displacement mechanism 16a through tube 85. Motor 63 engages portion 92 with portion 96 with enough force to keep pipet tip 80 on mandrel 58 and to form an air seal so that pipeting action can be accurately controlled by air displacement mechanism 16a. Preferably, though, by limiting the current to motor 63, motor 63 is enabled to drive mandrel 58 to engage pipet tip 80 with less than all of the motor's force so that the pipet tip can later be stripped from mandrel 58 by motor 63.

Pipet air assembly 16a, FIG. 2A, includes piston assembly 82 with piston 83 driven in the direction of the arrow by stepper motor 84. By proper control of motor 84, mechanism 82 is enabled to deliver to or withdraw from pipet tip 80 a controllable volume of air, thus providing the device with the ability to withdraw and dispense controlled amounts of fluid through opening 98.

Figure 2B:
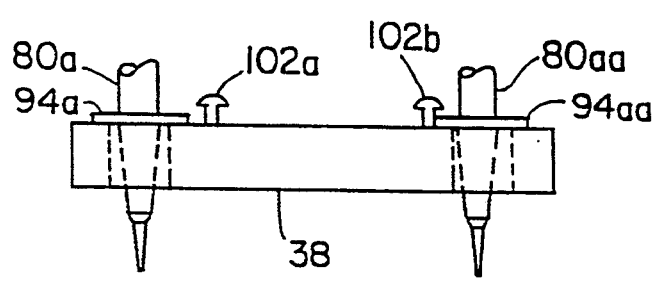
FIG. 2B is a side view of an embodiment of the pipet tip rack and means for removing the pipet tips from the pipet arm of the device of FIG. 1A.

The pipet tip stripping action is illustrated in FIG. 2B, in which pipet tip 80a having enlarged annular portion 94a is shown in its ready-for-withdrawal position, in which portion 94a can be lifted past enlarged head stop mechanism 102a, which may be a pin or screw. Second pipet tip 80aa is shown in the tip-stripping position in which enlarged annular portion 94aa is below the head of mechanism 102b; when a pipet tip is in this position, and mandrel 58 is moved away from the pipet tip carousel by motor 63, portion 94aa catches under the enlarged head of mechanism 102b and the force of motor 63 withdraws mandrel 58 from tip 80b. This stripping mechanism thus provides the ability to strip pipet tips without having the separate stripping mechanism commonly used in automatic pipeters, for example a moving fork mechanism which engages the pipet mandrel above the pipet tip, and then pushes the pipet tip off the mandrel. By employing pipet tips with enlarged annular portions 94aa, and properly positioning stripping assemblies 102 in pipet tip rack 38, the pipet tips of the device of this invention may be stripped without having this type of separate stripping mechanism, and also without having a stripping mechanism which contacts mandrel 58 each time a pipet is stripped, thereby preventing the mandrel wear associated with these prior art stripping mechanisms.

Figure 2D:
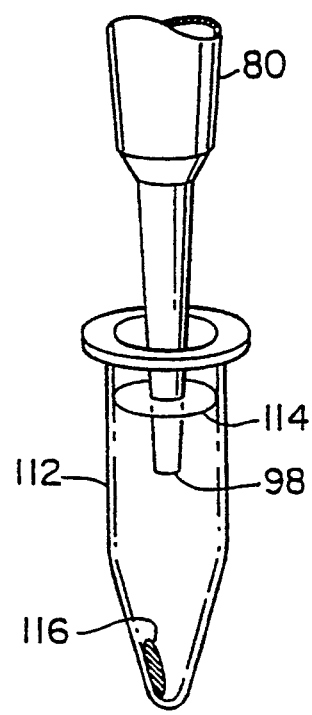
FIG. 2D shows a piper tip inserted in a cell tube to illustrate one method of fluid withdrawal according to this invention.
Figure 2C:
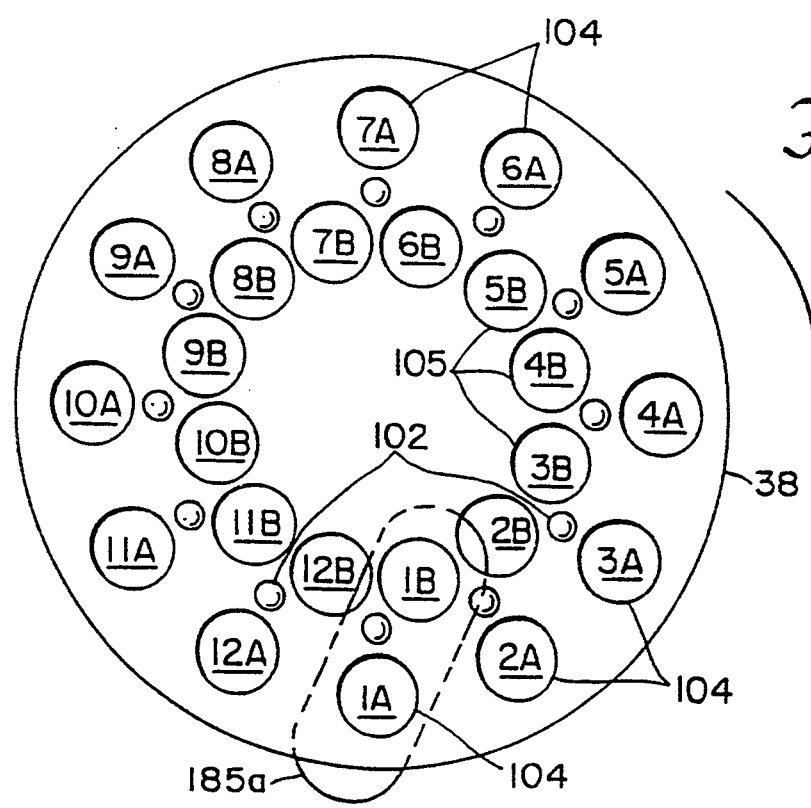
FIG. 2C is a top plan view of an embodiment of the pipet tip rack and centrifuge rotor of FIG. 1B.
Figure 2C:
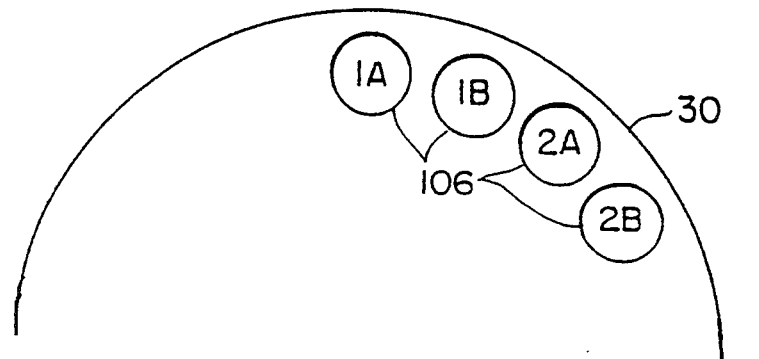

FIG. 2C illustrates partially centrifuge rotor 30 and pipet tip rack 38. Pipet tip receiving channels 104, labelled 1A, 2A, 3A, through 12A, each have associated therewith a stripping device 102. Inner ring 105 of pipet tip receiving channels, 1B through 11B, are each associated with two adjacent stripping devices 102; the receiving channels are slightly larger than the pipet tips to allow the tips to be properly positioned in relation to stripping heads 102 as shown in FIG. 2B. Rotor 30 includes sample tube receiving channels 106, also labelled 1A, 1B, 2A, and 2B, and so on. Positions 1A and 1B are in the home or pipet pick-up positions located under the pipet arm. Funnel 185a leading to waste receiving container 33, FIG. 1B, is positioned below the pipet tip rack home position to allow dispensing of waste. By employing the position sensors and indexing drive described above, rotor 30 and carousel 38 are driven to maintain a predetermined alignment of the pipet tip and sample tube receiving channels to insure that each pipet tip is used with the desired sample tube. The receiving channels are labelled A and B in reference to a preferred embodiment described below, in which two sample tubes, and consequently two pipet tips, are used for each cell sample, although this is not a necessary limitation of the invention.

FIG. 2D illustrates in detail the placement of pipet tip opening 98 in relation to sample tube 112. In withdrawing fluid from tube 112, opening 98 is enabled to be placed at a desired position in relation to meniscus 114 to allow the fluid to be withdrawn in a desired fashion. In the example shown, where debris pellet 116 is found in the bottom of tube 112, opening 98 is preferably placed just below meniscus 114. Then, as the liquid is withdrawn, pipet tip 80 is moved down toward the bottom of tube 112 to maintain the position of opening 98 just below meniscus 114 in order to remove the fluid without disturbing debris 116. Alternatively, opening 98 can be placed where desired in tube 112 and enabled to sustain that position during the liquid withdrawal, as will be more fully described below.

Figure 2E:
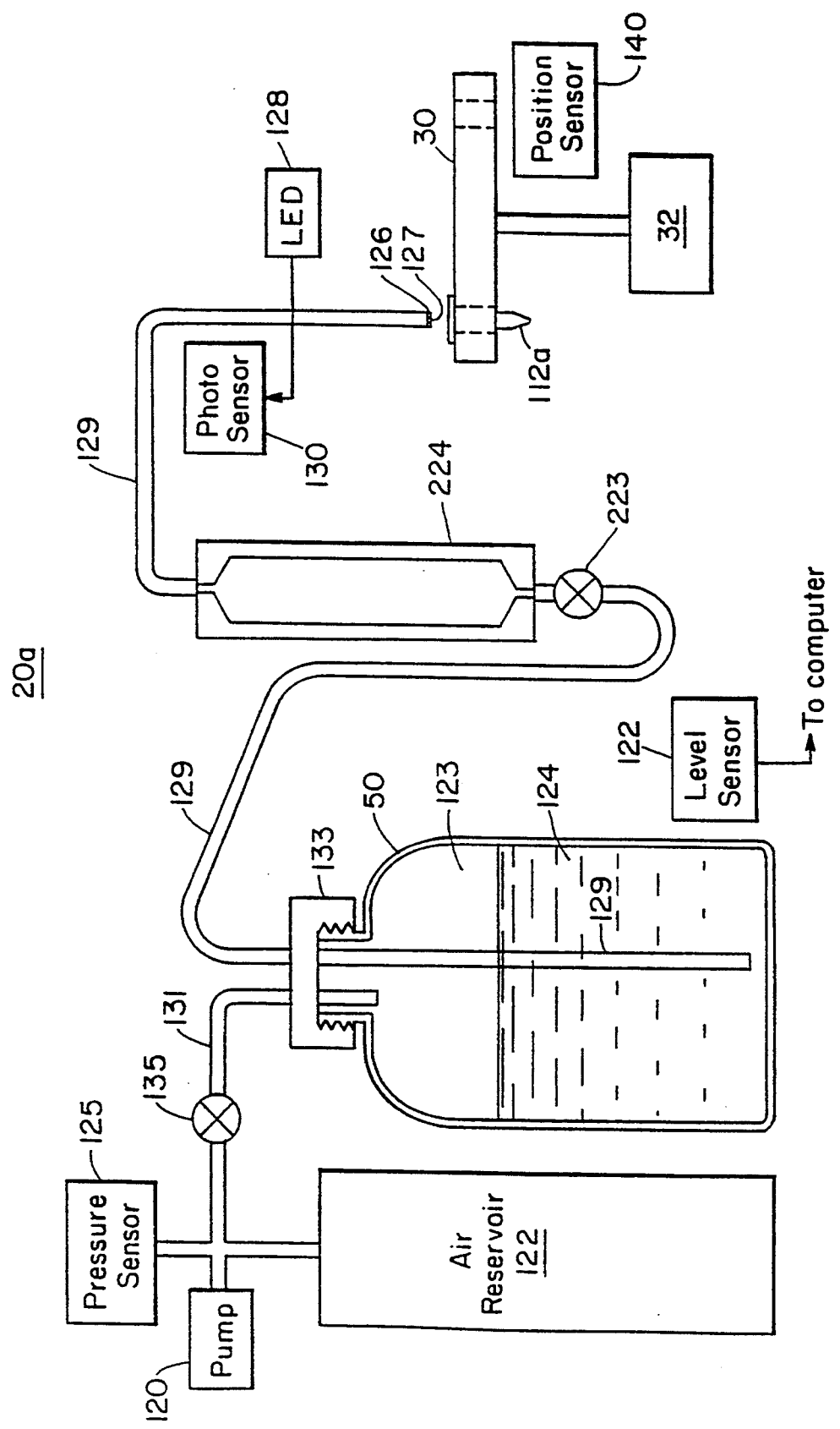
FIG. 2E is a more detailed schematic diagram of an embodiment of the reagent add system and centrifuge position sensor of FIG. 1A.

Reagent add assembly 20a is shown in detail in FIG. 2E. Assembly 20a moves reagent 124 from reagent bottle 50 to sample tube 112a, and also determines the amount of reagent in bottle 50, as follows. Some time after the nucleic acid separation device is enabled, air pump 120 fills reservoir 122 with a predetermined air pressure sensed by sensor 125. Valve 135 is then opened to equilibrate the air pressure in reservoir 122 and empty bottle space 123. Since the volume of reservoir 122 and bottle 50 are known, the volume of empty space 123 can be calculated based on the pressure drop sensed by sensor 125. The system then determines the volume of reagent 124 in bottle 50 by subtracting volume 123 from the volume of bottle 50. Alternatively, physical liquid level sensors such as sensor 122 may be employed to determine reagent levels. This reagent volume analysis system thus allows the separation device to insure before the separation begins that sufficient reagent is available to fully perform the desired separation technique, thereby preventing any incomplete separations due to insufficient reagent. Preferably, the device computer is enabled to indicate a "reagent low" warning when the reagent bottle is almost empty, and a "reagent empty" signal is employed, combined with preventing the operation of the device, when there is insufficient volume of any one of the reagents being used.

Presuming enough reagent is present, reagent is transferred from bottle 50 to sample tube 112a as follows. Pump 120 provides a predetermined air pressure to bottle 50 through line 131 to force liquid up through line 129 toward tube 112a. Cap 133 seals bottle 50. Orifice plate 126 is placed in line 129, and has an opening 127 of a known and precise diameter for exactly controlling the liquid flow rate to allow precise control of the volume of reagent supplied to sample tube 112a. LED or other radiation source 128 is disposed proximate the end of line 129 for indicating when line 129 is fully primed by employing photosensor 130, which detects a change in transmitted radiation intensity when the liquid reaches this part of tube 129. Depending on the reagent, the transmitted intensity can be decreased by absorption or increased by focusing caused by the reagent index of refraction. Signal sensitivity may be optimized by relative locations of the light source, light sensor, and the axis of the fluid channel. Preferably, the priming operation takes place before any reagent is added, for precise control of reagent add volume. Enlarged diameter vertical bubble trap 224 is included in line 129 to allow any air bubbles in the line to escape before the fluid reaches orifice 126 to provide effective priming. Solenoid valve 223 is then used to control reagent delivery to sample tube 112a.

By using a known reagent supply pressure, and orifice 126, the flow rate of reagent to tube 112a is fixed. Thus, the volume of reagent to be added is controlled simply by controlling the reagent add time. Preferably, to prevent spillage of reagent, after a reagent add has been completed to each of the sample tubes in the centrifuge rotor, pump 120 is enabled to withdraw the reagent from feedline 129 back into bottle 50. Then, when the reagent is next used, line 129 is primed again. Also illustrated is rotor position sensor 140, used to position tube 112a as desired, for example under reagent delivery opening 127.

The process variables for a preferred separation technique employing the device of this invention are illustrated in FIGS. 3A and 3B. Commands 1 through 15 are each of the commands necessary to enable system 10 to automatically perform all of the steps necessary to prepare biomolecules, more particularly to separate nucleic acid from cell samples. The use of these commands is illustrated in the process steps for a preferred separation protocol illustrated in FIGS. 5A through 5C.

The "spin centrifuge" command allows the user to establish centrifuge rotation time and speed in rpm. The "add reagent" command allows the user to input the reagent reservoir to be used, indicated as A through L, the reagent add volume in microliters, and the sample tube, A, B or C, to which the reagent is to be added. The "pipet mix" command allows the user to mix the tube samples by repeated drawing of the liquid in and out of the pipet tip. The user inputs which tube contains the sample to be mixed (A, B or C), and how far into the tube the tip is to be placed. This pipet position is indicated in microliters from the bottom of the tube instead of a measured distance; the computer translates this volume measurement to an axial distance using the known relationship between tube volume and meniscus height above the bottom of the tube.

The other variables are the volume that is to be drawn into and out of the tip in microliters, the pipet rate in microliters per second, and the number of repetitions to be performed. This pipet mixing may be performed by pipet air assembly 16a, FIG. 2A, for example. Alternatively, cell sample tube contents may be mixed by gently agitating the centrifuge rotor back and forth one or more times employing motor 32, FIG. 1B.

Another alternative means of mixing the sample tube contents is the "bubble mix" command, employing the same variables as the "pipet mix" command, except the sample is not drawn into the pipet tip. Instead, air is blown through the pipet tip into the sample by the pipet air mechanism. This is a more gentle way to mix the sample which minimizes shear forces in the solution as desired. If the amount of air to be blown is greater than the volume of cylinder 82, FIG. 2A, the pipet tip may be withdrawn from the liquid and piston 83 backed off to allow another volume of air to be dispensed.

The "pick pipet" command allows the user to pick up a pipet tip from the pick pipet position (1A or 1B, FIG. 2C) of the pipet tip rack. The "park pipet" command allows the user to deposit the pipet tip in use back into the tip rack; this command does not require any variable parameter since only one pipet tip is in use at a time.

The "withdraw" command allows the user to withdraw fluid from the sample tube. The variables provide the ability to set the initial pipet position (the depth the tip is to be placed in the tube at the start of withdrawal), as well as a withdrawal mode, which indicates whether the pipet position is to be held fixed during the withdrawal, or is to vary during the withdrawal. When the fixed mode is chosen, the tip is caused to dive to the indicated depth, and the liquid is withdrawn. When the variable mode is chosen, the tip moves to the indicated starting depth and begins withdrawing the liquid. The tip is then caused to move further into the tube to keep the tip just below the meniscus while pipeting. This mode is useful for pipeting liquids at an interface at a particular depth in the tube, with minimal disturbance of the interface.

The "dispense" command allows the user to dispense liquid contained in the pipet tip to a certain tube, using the variables indicated. The "puff" command allows the user to blow off any droplets that form at the end of the pipet tip after dispensing; the command causes the pipet air mechanism to displace the chosen volume of air through the tip. Often, the "wait" command, command number 11, is chosen to precede the "puff" command to allow the liquid to drain down to the tip of the pipet before it is puffed out of the pipet; the "wait" command has been chosen to allow the user to insert short pauses in the separation protocol wherever desired. Preferably, a preselected time period, for example 55 milliseconds, is chosen as a base time period, and the "wait" command allows the choice of a desired number of those time periods. For example, "wait (1)" would cause a delay of 55 milliseconds.

The "dispose of fluid" command allows the user to discard pipeted liquids into a waste container located below the home position of the pipet tip carousel, shown as reservoir 185a, FIG. 2C. The "delay" command, input as seconds, allows the user to insert long pauses in the protocol. This command is useful, for example, when an incubation of several minutes duration is required at a certain point in the protocol. The "begin" command is used to indicate the beginning of a series of commands which are to be performed on each sample, and the "next sample" command is used to indicate the end of that set of commands being performed on each sample. Thus, commands bracketed by "Begin" and "Next-Sample" are performed on each sample, typically tube set A or tube set B. The "overlap" command allows the user to enable the device to perform two functions at once, for example centrifuging and priming reagent lines.

Figure 4:
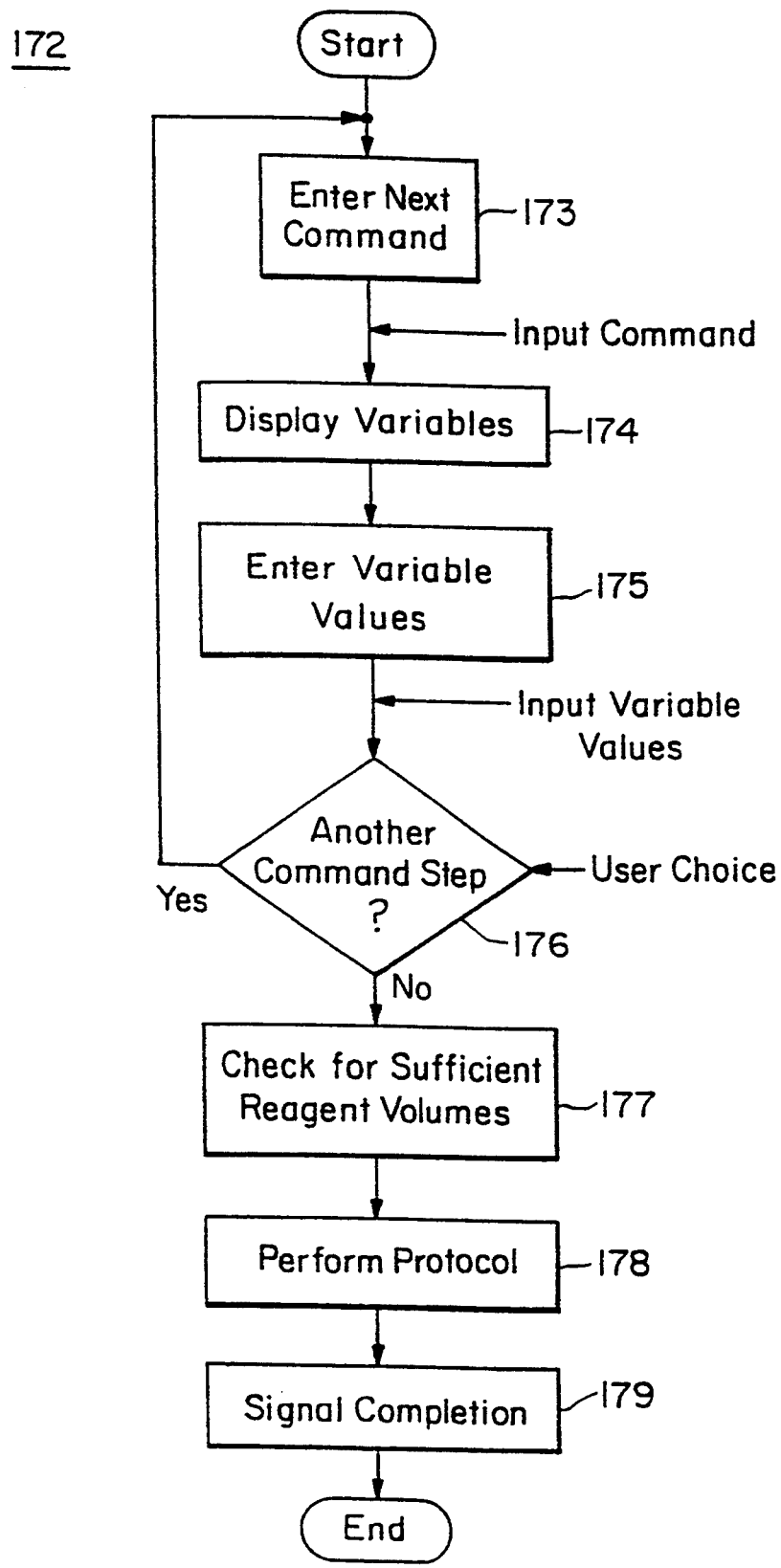
FIG. 4 is an embodiment of operating software for the device of FIG. 1A.

FIG. 4 illustrates an embodiment of operating software 172 for the device according to this invention. At step 173, the system prompts the user to enter the next command in the sequence of commands the user is employing to accomplish a desired biomolecule preparation. In response, the user inputs the desired command, and the system at step 174 then displays the variables associated with that command, shown in FIGS. 3A and 3B. At step 175 the system prompts the user to enter the variable values, and then moves to step 176, in which if there is another command step, the operation loops back to step 173. If the last command has been entered, the system at step 177 checks for sufficient reagent volumes in the reagent bottles to be used in the preparation technique, and then performs the protocol, step 178; completion is then signalled, step 179. Alternatively, the device may be pre-programmed with several preparation protocols such as that described below, in which case the user simply chooses which protocol is to be performed. Another alternative is to allow the user to program the system by writing the program on a separate computer and then inserting the program into the memory of the device.

Figure 5B:
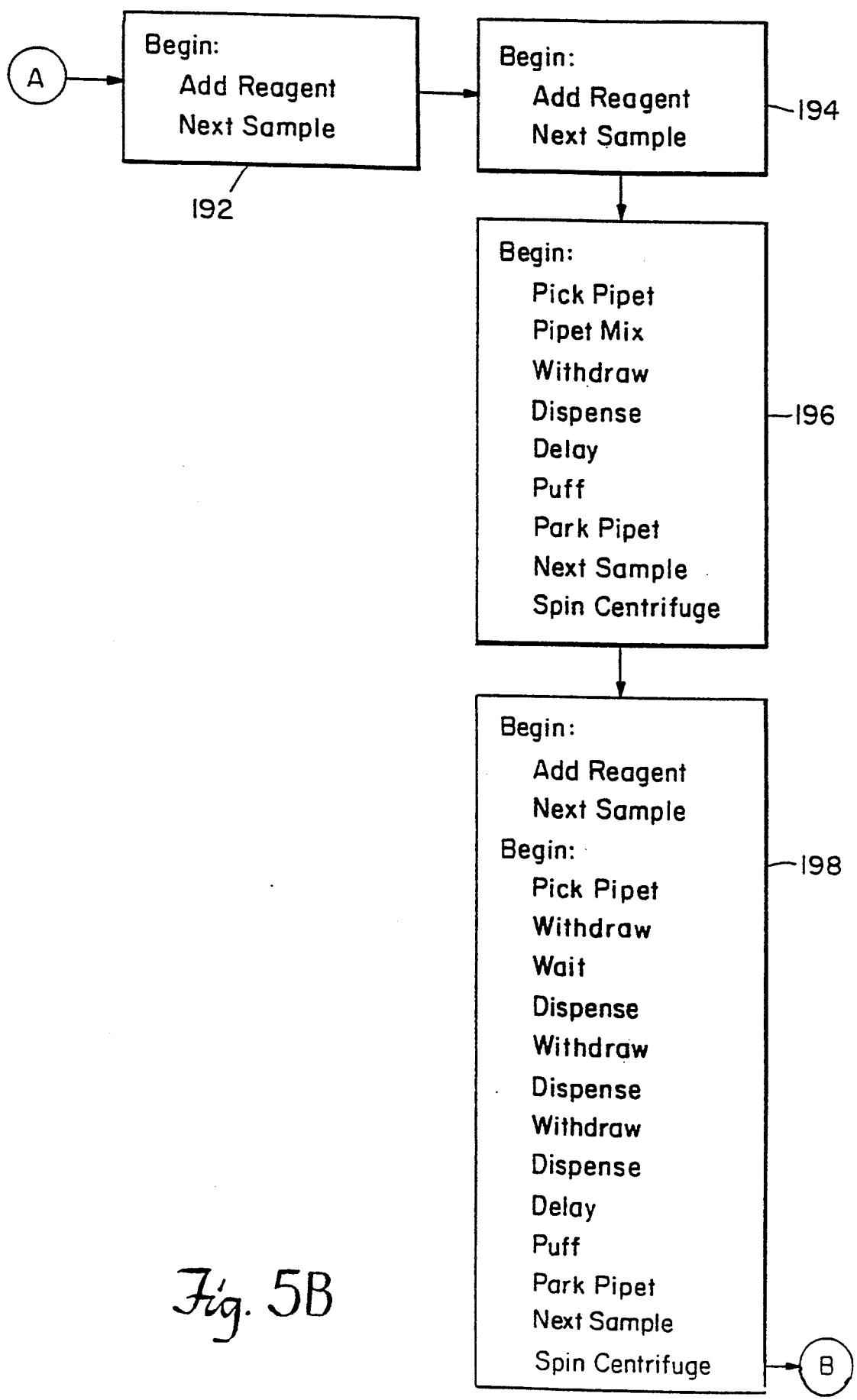

A single preparation protocol 180 which has been successfully employed to separate DNA from cell cultures in broth medium is illustrated in FIGS. 5A through 5C. This protocol employs the commands illustrated in FIGS. 3A and 3B, but is merely one example of a biomolecule preparation protocol which may be accomplished with the device according to this invention; the protocol is exemplary and in no way limits the invention. The first step in protocol 180 is to pellet the cell samples by centrifugation, step 184. Two minutes at 4,000 rpm is sufficient. At step 186, the nutrient broth is removed from the tubes and discarded to waste.

Step 186 has as its first command the "begin" command, and as its last the "next sample" command. As a result, the intermediate command steps are performed for each cell sample tube in the centrifuge rotor. In a preferred embodiment, the rotor includes twenty-four sample slots for processing twelve cell samples; each sample requires a first tube, A, holding the cells in the broth medium, and a second, initially empty tube, B, which will eventually hold the resuspended DNA. Step 186 begins with the device picking pipet A and withdrawing the broth in two withdrawal steps, the first being in the variable mode to carefully remove most of the broth, and the second being a final removal of a small amount of remaining broth with the tip fixed in position near the pelleted cell sample. After waiting for one time period, the withdrawn fluid is disposed of, there is a delay of one second, and then a puff to blow off the small drop of broth remaining on the pipet tip. The pipet tip is then parked. Operation would then proceed back to the pick pipet step at the beginning of process step 186, at which time the pipet tip carousel and the centrifuge rotor would each be indexed to present the next pipet tip and the next sample tube.

After the broth has been removed from all the sample tubes, an isotonic buffer is added, step 188. In step 190, the cell pellet is resuspended in the buffer by pipet mixing. This process step includes the steps of picking pipet A, pipet mixing the buffer/cell mixture, and then dispensing any fluid remaining in the pipet tip and puffing off any drops left thereon. The pipet is then parked so that the operation can proceed to the next pipet and the next sample.

Step 192 is a second reagent add; this may be a reagent which lyses and denatures the cells. A third reagent, to deproteinate and neutralize the samples, is then added at step 194. At step 196, the contents are mixed by pipeting, and then centrifuged at 9,000 rpm for two minutes. This step also illustrates that since all of the samples are centrifuged at the same time, the "spin centrifuge" command comes after the "next-sample" command. The "pick pipet" through "park pipet" commands are bracketed by a "Begin" and "Next-Sample" so that step 196 in total accomplishes a mixing of all twelve cell samples. The mixing is accomplished by picking the pipet and pipet mixing the sample, and then withdrawing and dispensing fluid followed by a delay, puff, and park pipet command.

Step 198 accomplishes the precipitation of DNA in the second sample tube B by first adding a precipitating reagent to tube B, and then transferring the supernatant in tube A to tube B with pipet B by picking the pipet, withdrawing the supernatant from tube A in the variable mode, and then dispensing and withdrawing in tube B a number of times to mix the supernatant with the precipitating agent, followed by the delay, puff and park pipet steps. The DNA is then pelleted in all of the sample tubes by spinning the centrifuge at a high speed of 9,000 rpm for three minutes.

The next step, 200, accomplishes the purification of the pelted DNA by first picking pipet B. The supernatant is then discarded from all of the sample tubes with that single pipet tip by withdrawing the supernatant in the variable mode, disposing of the fluid, and emptying the pipet with the delay and puff steps. A single tip may be used to withdraw the supernatant from all tubes because the DNA is pelleted, so cross-contamination is not a concern. The use of a single pipet tip saves process time, but is not required for successful DNA separation.

The DNA pellet is then washed with a further reagent by adding the wash reagent to all of sample tubes B, and then withdrawing and discarding the reagent by withdrawing most of the fluid in the variable mode, and then moving the pipet tip to the bottom of the tube and withdrawing the remainder of the fluid, disposing of the fluid, and puffing off the fluid to clean the pipet. The pipet is then parked and operation proceeds to the final step, 202, in which the DNA pellet is air dried by centrifuging for two minutes at a low speed of 4,000 rpm to swirl the air through the tubes to fully evaporate the alcohol wash reagent from the tubes. A buffer reagent is then added to resuspend the DNA, and operation is complete.

This separation protocol is but one that can be performed by the device of this invention. An example of a protein preparation protocol which can be performed contemplates detaching peptides synthesized on a support matrix by adding an acid to release the peptides, and centrifuging to pellet the matrix material (e.g. latex beds). The peptide may then be transferred to a second tube and concentrated with ethanol.

Thus, the device has the capability of preparing biomolecules from samples automatically and precisely, without the need for human intervention, thus dramatically decreasing the cost per successful preparation.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A self-contained biomolecule preparation device for automatically preparing biomolecules such as nucleic acid from samples such as cell samples, comprising:

a plurality of samples tubes contained in a rotor for holding chemical compounds in liquid or solid form;

a plurality of pipet tips to withdraw and dispense controlled amounts of fluid contained in said plurality of sample tubes;

a centrifuge, containing the rotor, for spinning said plurality of samples tubes in said rotor at predetermined times;

a pipet tip rack, separate from the centrifuge and the rotor, for holding said plurality of pipet tips, each of said tips associated with and substantially parallel to one of said sample tubes in the rotor of said centrifuge;

means for maintaining a predetermined relationship between the pipet tips in said tip rack and the sample tubes in the rotor;

a pipet arm assembly, proximate said pipet tip rack and the rotor of said centrifuge, including a pipet tip handling mandrel, driven to move in two dimensions by a motorized mechanism, for selectively removing pipet tips from said pipet tip rack, inserting them into the sample tubes in the rotor of said centrifuge, and returning the selected pipet tip back to the tip rack for further use, said arm assembly responsive to said means for maintaining so that the pipet tip selected for removal remains associated with the sample tube in which the pipet tip is to be inserted;

a plurality of reagent reservoirs, proximate said sample tubes, for holding biomolecule preparation reagents;

reagent adding means for selectively adding controlled amounts of the reagents from said reservoirs to said sample tubes at predetermined times;

mixing means for mixing the sample tube contents at predetermined times;

fluid withdrawal means for withdrawing fluid from a sample tube into an inserted pipet tip at predetermined times; and process control means for controlling the operation, including the integrated sequence of operations, of said centrifuge, said pipet arm, said reagent adding means, said mixing means and said fluid withdrawal means.

2. The biomolecule preparation device of claim 1 in which said mixing means includes means for agitating the rotor.

3. The biomolecule preparation device of claim 1 in which said mixing means includes means for passing air through the pipet tip inserted in the sample tube to bubble air in the fluid.

4. The biomolecule preparation device of claim 1 in which said pipet arm assembly includes a stepper motor for controllably inserting said pipeting end into the pipet tips.

5. The biomolecule preparation device of claim 1 further including centrifuge rotor control means for controlling the speed and duration of rotation of the rotor of said centrifuge.

6. The biomolecule preparation device of claim 1 in which said process control means includes a system of operating software for prompting the user to select process commands and variables to automatically produce DNA from cell samples.

7. The biomolecule preparation device of claim 1 further including tip stripping means containing a stripping structure proximate each pipet tip position in said pipet tip rack for stripping a pipet tip from said pipet arm assembly.

8. The biomolecule preparation device of claim 1 in which said mixing means further includes means for repeatedly drawing fluid in and Out of the pipet tip inserted into a sample tube.

9. The biomolecule preparation device of claim 8 in which said mixing means further includes means for controlling the fluid flow rate.

10. The biomolecule preparation device of claim 1 further including reagent volume determining means for determining the reagent volume in said reagent reservoirs.

11. The biomolecule preparation device of claim 10 in which said reagent volume determining means includes means for supplying a known volume of gas at a known pressure to said reservoir.

12. The biomolecule preparation device of claim 10 in which said reagent volume determining means includes a liquid level sensor.

13. The biomolecule preparation device of claim 1 in which said pipet arm assembly includes a passive insertion control means for controlling the depth of insertion of the pipet tip into the sample tube.

14. The biomolecule preparation device of claim 13 further including liquid level determining means for determining the liquid level height in the sample tube.

15. The biomolecule preparation device of claim 14 in which said insertion control means is responsive to said liquid level determining means for placing the pipet tip at a desired position in relation to the tube liquid surface.

16. The biomolecule preparation device of claim 1 in which said reagent adding means includes a reagent delivery orifice for delivering reagents at a predetermined flow rate.

17. The biomolecule preparation device of claim 16 in which said reagent adding means further includes reagent pressure control means for controlling the reagent pressure for delivering reagent through said orifice at a controllable rate.

18. The biomolecule preparation device of claim 17 further including means for establishing the reagent delivery period to control the volume of reagent added.

19. The biomolecule preparation device of claim 1 in which said reagent adding means includes a liquid delivery conduit from said reservoirs leading to proximate the rotor of said centrifuge.

20. The biomolecule preparation device of claim 19 in which said reagent adding means further includes reagent sensing means for sensing the presence of reagent proximate the end of said delivery conduit.

21. The biomolecule preparation device of claim 20 in which said reagent sensing means includes means for determining a change in light intensity transmitted through said conduit.

22. The biomolecule preparation device of claim 19 in which said delivery conduit further includes a bubble trap to allow air bubbles entrapped in the reagent to escape.

23. The biomolecule preparation device of claim 22 further including means for withdrawing reagent from said conduit after reagent delivery to prevent reagent spillage.

24. The biomolecule preparation device of claim 1 in which said means for maintaining includes position control means for controlling the relative positions of the rotor of said centrifuge and said pipet tip rack.

25. The biomolecule preparation device of claim 24 in which said position control means includes means for determining the position of the pipet tip rack.

26. The biomolecule preparation device of claim 25 in which said position control means further includes means, responsive to said means for determining, for rotating said pipet tip rack.

27. The biomolecule preparation device of claim 26 in which said means for rotating includes a stepper motor for indexing said pipet tip rack.

28. The biomolecule preparation device of claim 24 in which said position control means includes means for determining the position of the rotor.

29. The biomolecule preparation device of claim 28 in which said position control means further includes means, responsive to said means for determining, for rotating the rotor.

30. The biomolecule preparation device of claim 29 in which said means for rotating includes a motor for spinning or indexing said rotor.

31. The biomolecule preparation device of claim 29 in which said reagent adding means includes at least one reagent dispensing opening fixed in relation to the rotor to allow positioning of a selected sample tube below a selected dispensing opening.

32. The biomolecule preparation device of claim 29 in which said means for rotating includes a detent position for each rotor sample tube location.

33. The biomolecule preparation device of claim 32 in which said means for rotating includes a brushless DC motor.

34. The biomolecule preparation device of claim 24 in which said means for maintaining includes means for aligning a selected pipet tip with a selected sample tube.

35. The biomolecule preparation device of claim 34 further including means for moving said pipet arm in two axes, in and out of said rotor and pipet tip rack, and between said rotor and pipet tip rack.

36. The biomolecule preparation device of claim 35 in which said means for moving includes at least one stepper motor for controllably positioning the pipeting end.

37. The biomolecule preparation device of claim 36 in which said means for moving further includes means for sensing a predetermined position of said stepper motor.

38. The biomolecule preparation device of claim 1 in which said fluid withdrawal means includes an air cylinder operably connected to said pipet arm pipeting end.

39. The biomolecule preparation device of claim 38 in which said air cylinder includes a movable piston for varying the volume of said air cylinder.

40. The biomolecule preparation device of claim 39 further including piston control means for controllably moving said piston.

41. The biomolecule preparation device of claim 40 in which said piston control means includes a stepper motor.

42. The biomolecule preparation device of claim 42 further including piston sensing means for sensing a predetermined position of said piston.

43. A biomolecule preparation device for automatically preparing biomolecules such as nucleic acid from a sample such as a cell sample, comprising:
a plurality of sample tubes contained in as indexing sample tube rotor for holding chemical compounds in liquid or solid form;
a plurality of pipet tips to withdraw and dispense controlled amounts of fluid contained in said plurality of sample tubes;
a variable speed centrifuge, with an indexing sample tube rotor, for spinning said sample tubes at predetermined times;
tube position determining means for determining the position of the tube rotor with respect to the centrifuge to locate each sample tube in the rotor;
an indexing pipet tip rack, separate from the centrifuge and the tube rotor, for holding at least one said pipet tip for each sample tube;
said pipet tip rack holding said pipet tip substantially parrallel to said sample tube;
means for determining the position of the tip rack with respect to the centrifuge to locate each pipet tip in relation to a respective sample tube;
a pipet arm, proximate said indexing pipet tip rack and the rotor of said centrifuge, having a pipeting end;
first arm displacing means for displacing said pipeting end in a first direction coaxially into a pipet tip to engage the tip associated with said respective sample tube;
second arm displacing means for displacing said pipeting end in a second direction coaxially with the engaged pipet tip to withdraw the tip from said tip indexing tip rack;
tip insertion means for inserting the engaged pipet tip into said respective sample tube at predetermined times;
mixing means for mixing the tube contents by both repeatedly withdrawing at least part of the sample tube contents into the engaged pipet tip and dispensing the withdrawn tube contents back into the tube at predetermined times;
a plurality of reagent reservoirs, proximate said indexing sample tube rotor, for holding biomolecule preparation reagents;
a reagent dispensing orifice proximate said indexing sample tube rotor;
reagent dispensing means for dispensing under pressure reagent from at least one of said reservoirs through said orifice into the sample tube at a rate controlled by the orifice size and the dispensing pressure at predetermined times; and
reagent dispensing time means for establishing the reagent dispense time to control the volume of dispensed reagent.

* * * * *